(12) United States Patent
Khan et al.

(10) Patent No.: US 9,113,692 B2
(45) Date of Patent: Aug. 25, 2015

(54) COSMETIC APPLICATOR AND METHOD OF MAKING

(75) Inventors: Raheel Khan, Franklin Park, NJ (US);
Leona G. Fleissman, Ridgewood, NJ (US); Catholyn T. Griffiths, Phoenix, MD (US)

(73) Assignee: Avon Products, Inc., New York, NY (US)

( * ) Notice: Subject to any disclaimer, the term of this patent is extended or adjusted under 35 U.S.C. 154(b) by 720 days.

(21) Appl. No.: 12/183,136

(22) Filed: Jul. 31, 2008

(65) Prior Publication Data

US 2009/0032053 A1    Feb. 5, 2009

Related U.S. Application Data

(60) Provisional application No. 60/953,362, filed on Aug. 1, 2007.

(51) Int. Cl.
| | |
|---|---|
| *A45D 40/24* | (2006.01) |
| *A45D 40/00* | (2006.01) |
| *A61K 8/02* | (2006.01) |
| *A61Q 1/02* | (2006.01) |

(Continued)

(52) U.S. Cl.
CPC ............... *A45D 40/00* (2013.01); *A45D 33/38* (2013.01); *A45D 40/0087* (2013.01); *A61K 8/0208* (2013.01); *A61Q 1/02* (2013.01); *A61Q 19/00* (2013.01); *A45D 2200/1009* (2013.01); *A45D 2200/1036* (2013.01); *A45D 2200/1045* (2013.01)

(58) Field of Classification Search
CPC .............. A45D 2200/1009; A45D 2200/1018; A45D 2200/1027; A45D 2200/1036

USPC .......... 132/222, 221, 270, 320, 317; 427/212, 427/299; 206/823, 581; 15/209.1
See application file for complete search history.

(56) References Cited

U.S. PATENT DOCUMENTS

| | | |
|---|---|---|
| 4,650,672 A | 3/1987 | Yagita et al. |
| 4,747,782 A | 5/1988 | Campbell, Jr. |

(Continued)

FOREIGN PATENT DOCUMENTS

| | | |
|---|---|---|
| AU | 2008201728 A1 | 5/2008 |
| EP | 0314340 | 5/1989 |

(Continued)

OTHER PUBLICATIONS

Paul Brians, e.g./i.e., http://public.wsu.edu/˜brians/errors/e.g.html, Retrieved Nov. 15, 2012, p. 1.

*Primary Examiner* — Todd Manahan
*Assistant Examiner* — Brianne Kalach
(74) *Attorney, Agent, or Firm* — David M. Joyal; Joan M. McGillycuddy

(57) ABSTRACT

A cosmetic applicator and method of manufacturing same, wherein the cosmetic applicator is formed of a substrate and an application element comprising one or more application areas that are cohesively maintained on the substrate in a gapless, side-by-side formation in the presence of wet and/or dry binders. The substrate is subjected to a wetting agent that provides a better bind for the cosmetic slurries as they are printed onto their respective application area. The cosmetic compositions of each cosmetic application area may be different. Various cosmetic effects may be provided to end-users in a portable application.

22 Claims, 9 Drawing Sheets

(51) Int. Cl.
*A61Q 19/00* (2006.01)
*A45D 33/38* (2006.01)

(56) References Cited

U.S. PATENT DOCUMENTS

| | | | |
|---|---|---|---|
| 4,752,496 A | 6/1988 | Fellows et al. | |
| 4,878,775 A | 11/1989 | Norbury et al. | |
| 4,925,667 A | 5/1990 | Fellows et al. | |
| 4,952,400 A | 8/1990 | Tararuj et al. | |
| 4,995,408 A * | 2/1991 | Wallschlaeger | 132/320 |
| 5,137,040 A | 8/1992 | Iosilevich et al. | |
| 5,340,569 A * | 8/1994 | Elliott et al. | 424/63 |
| 5,554,414 A | 9/1996 | Moya et al. | |
| 5,647,941 A | 7/1997 | Gunderman et al. | |
| 5,690,130 A * | 11/1997 | Gunderman et al. | 132/319 |
| 6,190,730 B1 * | 2/2001 | Matsos et al. | 427/212 |
| 6,214,362 B1 | 4/2001 | Page | |
| 6,217,998 B1 | 4/2001 | Reinhardt et al. | |
| 6,312,181 B1 | 11/2001 | Joulia | |
| 6,335,005 B1 | 1/2002 | Muller et al. | |
| 6,432,535 B1 | 8/2002 | Noguchi et al. | |
| 6,528,073 B2 * | 3/2003 | Roulier et al. | 424/401 |
| 6,530,379 B2 | 3/2003 | Iosilevich | |
| 6,723,306 B2 | 4/2004 | Gueret | |
| 6,764,965 B2 | 7/2004 | Hsieh et al. | |
| 2001/0014313 A1 | 8/2001 | Roulier et al. | |
| 2002/0075429 A1 | 6/2002 | Fujioka et al. | |
| 2002/0175442 A1 | 11/2002 | Reeves et al. | |
| 2003/0036290 A1 | 2/2003 | Hsieh et al. | |
| 2004/0003753 A1 | 1/2004 | Matsuda et al. | |
| 2004/0011376 A1 * | 1/2004 | Michel et al. | 132/320 |
| 2004/0037858 A1 | 2/2004 | Mammone | |
| 2004/0236296 A1 * | 11/2004 | Ziltener et al. | 604/380 |
| 2005/0045292 A1 | 3/2005 | Lindsay et al. | |
| 2006/0088484 A1 | 4/2006 | Thevenet | |
| 2006/0088562 A1 * | 4/2006 | Brieva et al. | 424/401 |
| 2006/0144294 A1 * | 7/2006 | Misaki et al. | 106/401 |
| 2006/0233847 A1 * | 10/2006 | Mammone | 424/401 |
| 2006/0285913 A1 * | 12/2006 | Koptis | 401/205 |
| 2007/0020220 A1 * | 1/2007 | Osborne | 424/70.14 |
| 2007/0078561 A1 * | 4/2007 | Sansone | 700/233 |
| 2008/0245381 A1 | 10/2008 | Iosilevich | |
| 2008/0248262 A1 | 10/2008 | Iosilevich | |
| 2009/0053416 A1 | 2/2009 | Iosilevich | |

FOREIGN PATENT DOCUMENTS

| | | |
|---|---|---|
| JP | 9-187316 A | 7/1997 |
| JP | 63-27417 A | 2/1998 |
| JP | 2001278739 A2 | 10/2001 |
| JP | 2006-102541 A | 4/2003 |
| JP | 2006130194 A | 5/2006 |
| TW | M253256 U | 12/2004 |
| TW | 200628561 | 8/2006 |
| TW | 200638896 A | 11/2006 |
| WO | 0201982 A1 | 10/2002 |

* cited by examiner

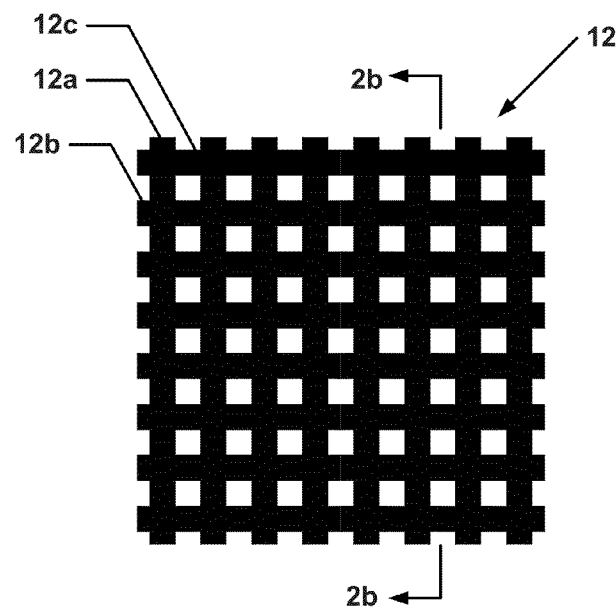
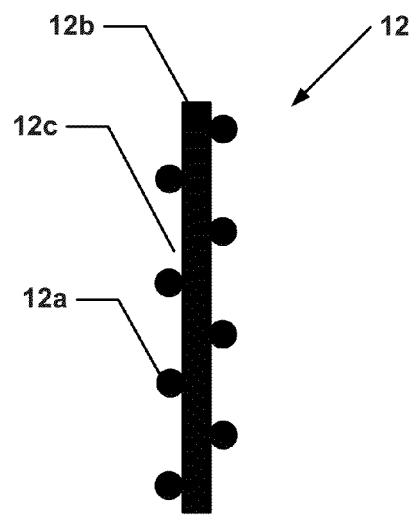
FIG. 2a          FIG. 2b
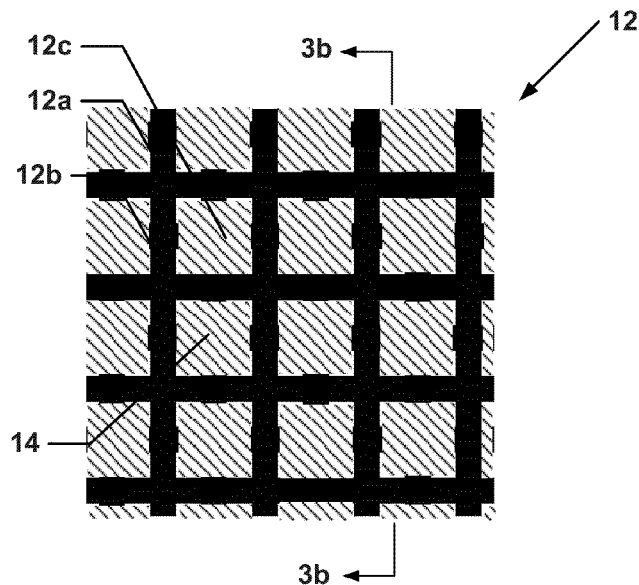
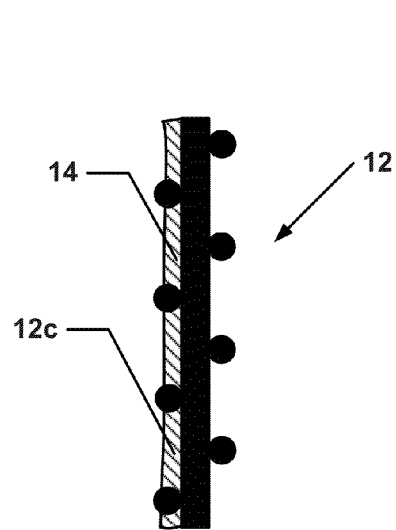
FIG. 3a          FIG. 3b

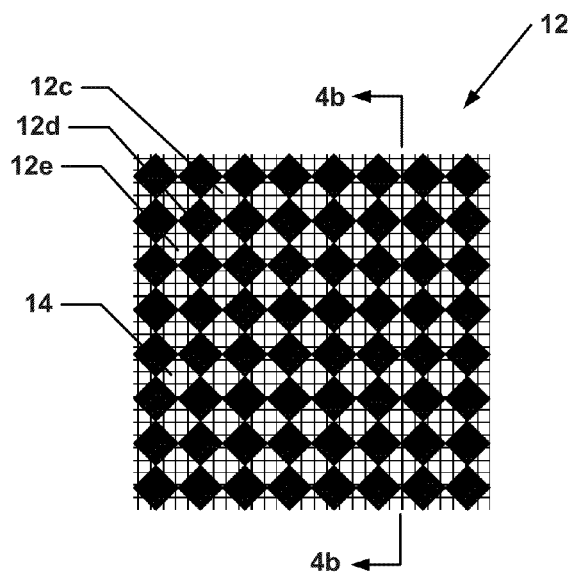
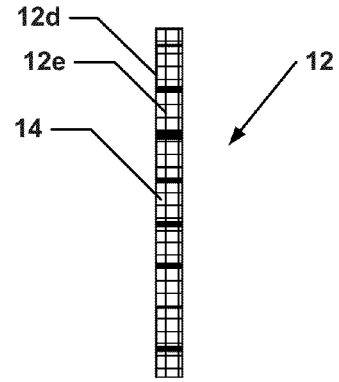
FIG. 4a    FIG. 4b
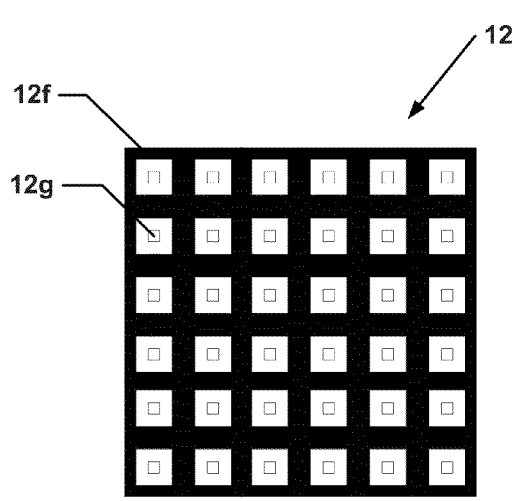
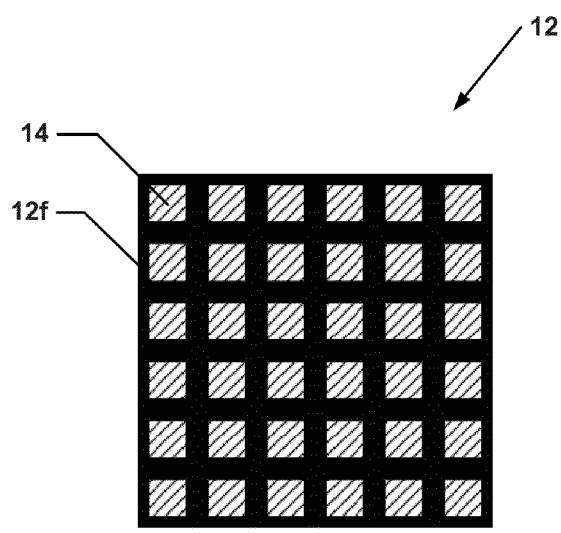
FIG. 4c    FIG. 4d

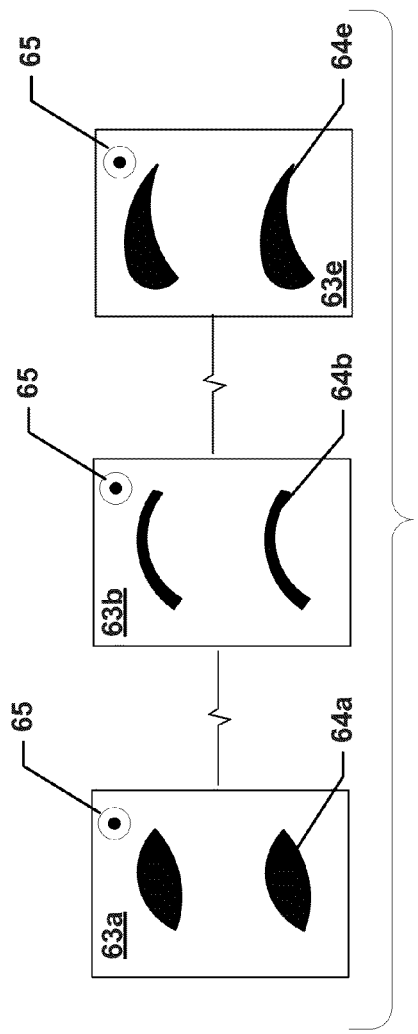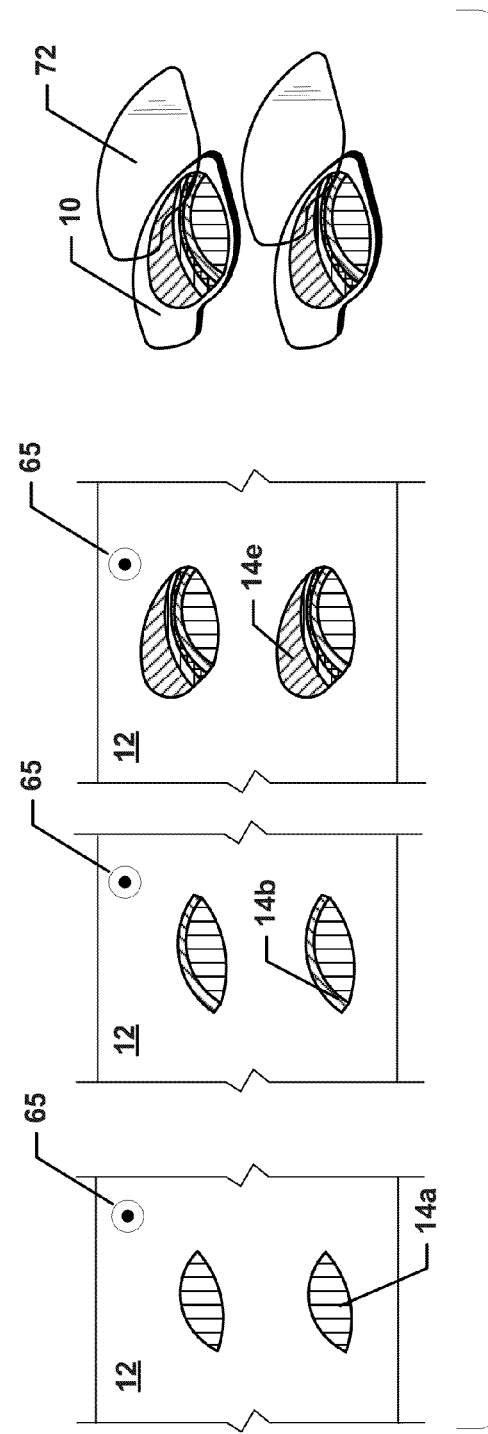

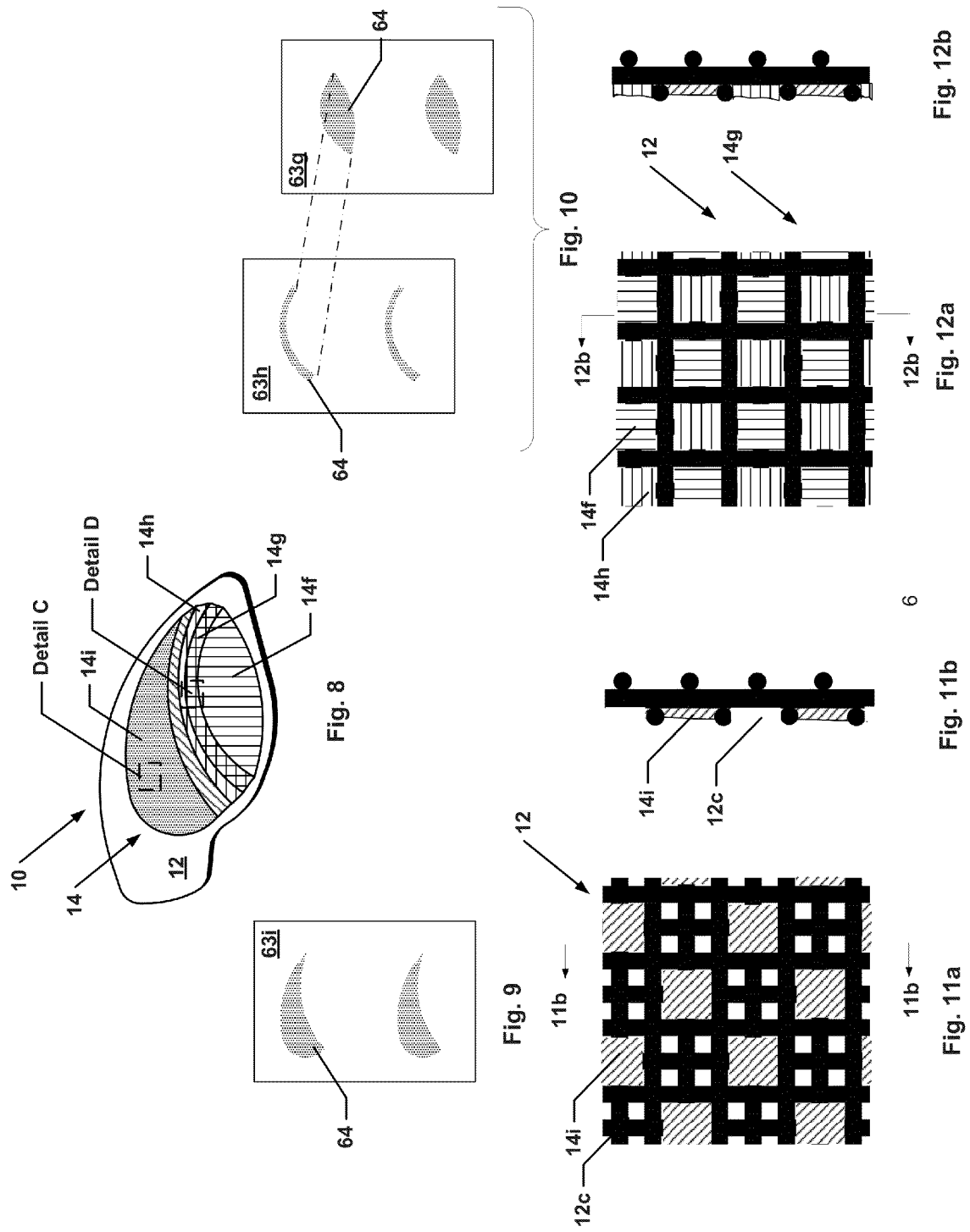

COSMETIC APPLICATOR AND METHOD OF MAKING

CROSS-REFERENCE TO RELATED APPLICATIONS

This application is non-provisional counterpart to, and claims priority from U.S. Ser. No. 60/953,362, filed Aug. 1, 2007, which is incorporated by hereby by reference for all purposes.

BACKGROUND OF THE INVENTION

The present invention relates to cosmetic items and, more particularly, to cosmetic applicators that transfer from a substrate to the human body.

DESCRIPTION OF THE RELATED ART

Applying cosmetics is, in general, a time-consuming experience for a user. However, applying cosmetics onto certain areas of the human body is an even more time-consuming task since these areas may require a more complex arrangement of cosmetics for the user to achieve a total look, i.e. a sophisticated polished look. Even given significant time, users often lack the necessary skill to create this look.

For example, in applying eye shadow, it is desirable to provide a darker shade on the eyelid and lighter shade proximate the eyebrow. The color is then blended from the crease at the eyelid, i.e. over the occipital bone, to proximate the eyebrow.

To achieve this look, a user must apply two or more primary shades of eye shadow via a utensil, such as a brush, wand, sponge, or the like. The intermediate color tones are achieved by blending these primary shades. Typically, this total eye make-up look requires an extremely skilled user or more likely a make-up artist. Thus, users desire a sophisticated look without the time-consuming effort.

In a further example, in applying lip make-up, the user begins by lightly outlining the lips with a sharp lip liner pencil in a shade close to that of the preferred lipstick color. To do so requires a steady hand and a technique that feathers the upper lip from the center to the corners of the mouth. For the lower lip, the lip is outlined from side to side. The lip is then filled in with a special base or balancer to even out the skin tones. Using lip stick or a lip brush, the color is then filled and blotted. Finally, a lip color is applied to obtain a preferred gloss look. Typically, this sophisticated look requires an extremely skilled user with sufficient time. Thus, users desire a sophisticated look without the time-consuming effort.

In yet another example, to cover a scar, several tones of color are blended to provide a natural look over a discrete area. A user typically does not have the skills to repeat the same blend day after day. Thus, a need exists for suitable and repeatable look.

Existing products in the art use an oily formula. Inherently, these products compromise quality and bleed color tones from one area to another. This is especially true in the area of the eyelid where repeated movement and propensity for natural oils of the area cause significant degradation of wear quality. Thus, what is desired is a transferable cosmetic suitable for a cosmetic applicator that has improved wear quality.

BRIEF SUMMARY OF THE INVENTION

Consistent with various embodiments disclosed herein, a cosmetic applicator, kit, and method for producing same is disclosed. Under one embodiment, the cosmetic applicator comprises a flexible material, such as paper, that pre-wetted with a wetting agent. Once wetted, the flexible material is provided with a first pattern using a first cosmetic slurry. Second and further patterns can then be provided on the formed flexible material using second and further cosmetic slurries, where the second and further patterns are immediately adjacent to a respective previous pattern in a side-by-side configuration. The side edge of each pattern should contact, or slightly overlap, a side edge of a neighboring pattern. Cosmetic slurries used for adjacent patterns are preferably different, so that the cosmetic applicator provides a more sophisticated look when applied by the user. When the flexible material for the cosmetic applicator is processed, it is preferably mated with a carrier board for support under another embodiment.

Under yet another embodiment, when the wetting agent is applied to the flexible material, it is absorbed into the flexible material prior to screen printing. The wetting agent may be applied using a print screen, and the wetting agent may comprise of at least one volatile and at least one non-volatile material. After application, the wetting agent is subjected to a drying process to evaporate at least at part of the volatile material. Furthermore, after each cosmetic slurry has been printed, at least part of the respective cosmetic slurry may be evaporated before proceeding further.

BRIEF DESCRIPTION OF THE DRAWINGS

FIG. 2a illustrates a planar enlarged view principally in accordance with Detail A of FIG. 1.

FIG. 2b illustrates a cross-sectional view of FIG. 2a.

FIG. 3a illustrates a planar enlarged view principally in accordance with Detail B of FIG. 1.

FIG. 3b illustrates a cross-sectional view of FIG. 3a.

FIG. 4a illustrates a planar enlarged view principally in accordance with Detail B of FIG. 1 in accordance with one or more embodiments of the present invention.

FIG. 4b illustrates a cross-sectional view of FIG. 4a.

FIG. 4c illustrates a planar enlarged view principally in accordance with Detail A shown in FIG. 1 in accordance with a further embodiment of the present invention.

FIG. 4d illustrates a planar enlarged view principally in accordance with Detail B shown in FIG. 1, according to the embodiment of FIG. 4c.

FIG. 6 illustrates a planar view of a series of screens used in the manufacture of the cosmetic applicator in accordance with FIG. 5.

FIG. 7 illustrates a planar view of a series of cosmetic applicators during manufacture in accordance with FIG. 5.

FIG. 8 illustrates a cosmetic in accordance with one or more embodiments of the present invention.

FIGS. 9 and 10 illustrate planar views of screens used in the manufacture of the cosmetic applicator in accordance with FIG. 8.

FIG. 11a illustrates a planar enlarged view principally in accordance with Detail C of FIG. 8 in accordance with one or more embodiments of the present invention.

FIG. 11b illustrates a cross-sectional view of the embodiment shown in FIG. 11a.

FIG. 12a illustrates a planar enlarged view principally in accordance with Detail D of FIG. 8 in accordance with a further embodiment of the present invention.

FIG. 12b illustrates a cross-sectional view of FIG. 12a.

DETAILED DESCRIPTION OF THE INVENTION

Figure 1:
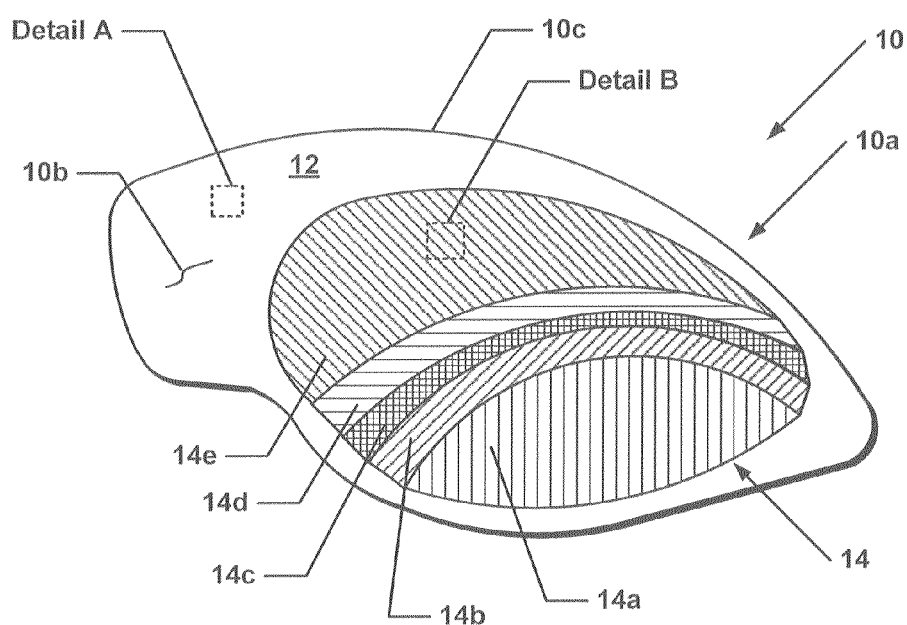
FIG. 1 illustrates a cosmetic applicator in accordance with in accordance with one or more embodiments of the present invention.

Referring to FIGS. 1-3, in accordance with one embodiment, a cosmetic applicator 10 includes a substrate 12, and an application element 14 that is deposited on the substrate and is suitable for transferring a plurality of cosmetic powder compositions utilized in the application element 14. The transfer of powder compositions could occur onto the body of a user, for example, when pressure is applied to the cosmetic applicator. The plurality of cosmetic powder compositions are preferably deposited on the substrate 12 of application element 14 in a predetermined configuration to provide a particular cosmetic effect.

While the cosmetic powder compositions have an affinity for the substrate 12, they have greater affinity to the skin, and accordingly are readily transferable from the substrate 12 to the skin. The application element 14 is intended to provide a unit dose of cosmetic to the skin of the user. Preferably, at least one of the transferable cosmetics has been formulated to have improved wear quality.

Herein, "cosmetic applicator" is used in the broadest possible sense for an article that transfers a cosmetic to the human body.

As used herein, "cosmetic" (or, synonymously, "cosmetic composition" and "cosmetic powder composition") means a composition in powder form, whether pigmented or unpigmented, that provides a desired visual cosmetic effect when topically applied as a thin layer on an area of the human body. For example, "cosmetic" may mean a blush, a face powder, or any other decorative or functional powder. In particular the cosmetic is suitable for use proximate the eyes, i.e., an eye shadow.

"Cosmetic" and "cosmetic applicator" also mean an article or a composition as the case may be that provides one or more therapeutic, medicinal, or holistic substances to impart a desired visual effect on the human body, including temporary, semi-permanent, or permanent effects on the human body.

"Unit dose" means an amount of cosmetic composition transferred to the skin sufficient for a single use of the applicator by the user and that provides a cosmetic effect to the area of application. Following the use of the applicator, the unit dose is depleted, and the applicator is discarded. While a unit dose is delivered to the user, the applicator may contain an excess of cosmetic over what is transferred to the skin of the user, i.e., there will be residual cosmetic on the substrate after use.

"Cosmetic effect" means a visible cosmetic enhancement to the area of the skin on which the cosmetic applicator has been used, which effect includes a plurality of different application areas, preferably of three or more, preferably three to five application areas, having different color shades.

Cosmetic applicator 10 preferably is configured to apply eye shadow to the eye area of a user as discussed above and as will be taught herein. However, cosmetic applicator 10 is not limited to this embodiment. For example, the cosmetic applicator may be configured to provide lip color, provide color to the cheeks, face, cover a scar or blemish, provide brows or enhance them.

It is noted that, under the embodiment involving a cosmetic application performed near the eye area and the like, certain challenges are introduced when compared to cosmetic applications performed on other parts of the human body. Specifically, the eye area is soft and supported only below the brow by a bone, the occipital bone. Thus, unlike the cheek where the cheekbone underlies the skin, cosmetic applicator 10 should be configured to be sufficiently soft and pliable.

To accommodate the bilateral symmetry of the human body, such as the eye area, cosmetic applicator 10 is suitably configured, under a preferred embodiment, to have a right and left version when needed to provide make-up to such areas of the human body. Thus, FIG. 1 shows a left version, and a right version would be a mirror image thereof. In a further embodiment, disclosed with respect to FIG. 13, to prevent mixing of a right or left applicator, an applicator is preferably configured to have a shape suitable for consecutive application to the left and right eye areas of a user. During application, the user would tear one of the applicator from the bridge area along, for example, perforations, and then apply the applicator as in other embodiments disclosed herein.

Since certain areas of the body, including the eye area, are difficult to align a cosmetic applicator to the intended area, the cosmetic applicator 10 is configured to have a shape 10a that is substantially suitable for the area of the body to which the cosmetic is to be transferred. Shape 10a may include a tab or handle 10b to permit easier positioning of the cosmetic applicator. The handle may be configured to be integral and substantially in the plane of the application element as shown in FIG. 1.

Typically, the user will hold handle 10b between a thumb and forefinger, such that cosmetic applicator 10 is disposed substantially within the plane formed between these two digits. Advantageously, when holding the cosmetic applicator 10 along a plane at areas of the body having an abrupt edge, such as the eye area proximate the temple, permits the user to more easily perceive the location of the cosmetic applicator and transfer a unit dose of the cosmetic.

Thus, when the user positions cosmetic applicator 10 to transfer the cosmetic, an edge surface of the cosmetic applicator, such as peripheral edge 10c, may contact the body of the user. The user will then be able to determine the position of cosmetic applicator 10 and make requisite corrections or confirm a correct position, based on prior learning and/or trial-and-error.

Handle 10b may also be formed separately. For example, handle 10b may be formed by having one or more portions attached to a side or a rearward surface of the cosmetic applicator. An additional portion of handle 10b may extend therefrom to permit a user to grasp handle 10b more conveniently. Handle 10b may then include one or more creases such that the handle can be folded and flat-packed with cosmetic applicator 10.

Substrate 12 preferably comprises a flexible planar body manufactured to encompass substantially the entirety of shape 10a to provide support to the application element. Substrate 12 is preferably made of a suitable material to receive the at least one cosmetic of application element 10. The material is preferably a soft, flexible paper that has sufficient tensile strength to withstand processing. The basis weight of the paper may be from about 4 to about 30 pounds, preferably about 8 to about 24 pounds. For an eyeshadow product the basis weight is preferably about 8 to about 16 pounds, and for a blush product the basis weight is preferably about 16 to about 24 pounds. Herein, basis weight means the weight of a 500 sheet (24"×36") ream.

Substrate 12 may alternately comprise paper including wax paper and silicone coated paper, floc, foam, non-woven or woven material, paper/fiber combinations, laminates, combinations thereof, or other suitable material that retains the at least one cosmetic and releases it when pressure is applied to a rearward surface of the applicator when the application element is in contact with the body of the user. Cellulosic paper is preferred.

Preferably, substrate 12 has a thickness suitable for generally maintaining shape 10a. When required, the substrate preferably bends sufficiently to follow one or more contours of the human body to which the cosmetic applicator is applied. When a paper substrate is used, typical thicknesses range from about 0.0010 to about 0.012 inches. In one embodiment thicker paper having a thickness of from about 0.0040 to about 0.012 inches can be used. Depending on processing conditions, this thicker paper may be adequate for making the cosmetic applicator in the absence of a support board or carrier. However, as described in further detail below, a thinner paper substrate may be used in conjunction with a laminated web or support board, in which case the paper thickness may be approximately between about 0.0010 to about 0.0040 inches, preferably between about 0.0010 to about 0.0030 inches, and most preferably from about 0.0012 to about 0.0025 inches.

In accordance with one embodiment illustrated in FIGS. 2a-2b and 3a-3b, substrate 12 may be formed of fibers 12a and 12b that are woven at an angle to each other as generally indicated with respect to Detail A, illustrated in FIG. 1. The fibers (12a, 12b) form one or more reservoirs 12c between the fibers for retaining one or more cosmetics of the application element in an area generally indicated as Detail B in FIG. 1.

In accordance with a further embodiment illustrated in FIGS. 4a and 4b, substrate 12 also may be formed of a non-woven material that has raised portions 12d and/or recessed portions 12e. One or more reservoirs 12c in the recessed portion or between the raised portions are thus formed for retaining one or more cosmetics of the application element in an area generally indicated as Detail B in FIG. 1.

In accordance with yet a further embodiment illustrated in FIGS. 4c and 4d, the substrate may also be formed of a non-woven material, such as a foam and/or a wicking material, that has raised portions 12f and pockets 12g providing a reservoir for retaining one or more cosmetics of the application element in an area generally indicated as Detail B in FIG. 1.

Application element 14 comprises a plurality of cosmetics disposed substantially in a thin layer on frontward surface of substrate 12. The application element comprises a pattern of one or more application areas, generally indicated as 14a-14e in FIG. 1. The application areas are preferably gaplessly adjacent to each other to comprise a coordinated effect or enhancement. The thin layer of cosmetic is configured to be cohesively maintained on the substrate in light of the presence of wet and dry binders, as disclosed below.

It is understood that each application area for application element 14 may have a cosmetic effect, such coloration or shade, when applied to the human body that, when considered as a whole, provides a sophisticated look. The shades and/or colors for each application area 14a-14e of application element 14 are preferably predetermined and suitably coordinated to permit ease of use for the user. Similarly, the size of each application area 14a-14e is preferably predetermined to provide a favored arrangement or to provide a coordinated effect and further permit ease of use for the user.

The quantity of cosmetic in each application area 14a-14e is preferably calibrated to deliver a suitable unit dose to the area to which each application area 14a-14e is applied. Since the skin of each user varies, the amount of cosmetic transferred from the applicator to the skin of the user may vary. Other factors may also influence the amount of cosmetic transferred, e.g., seasonal variations and other factors. The amount of cosmetic composition present in a unit dose is thus in excess over what is to needed to satisfy most situations and consumers.

For example, cosmetic applicator 10 may be configured to have one application area, such as area 14a, suitable for the eye area crease, and have one or more other areas of varying shade, i.e. areas 14b-14e extend on the eyelid to the lash line. Thus, three to five color shades in application areas 14a-14e may be present. Of these, one or more are distinct shades, for example, the shades of application areas 14a, 14c, and 14e and one or more are blended shades, i.e. the shades of application areas 14b (a blend of distinct shades 14a and 14c) and 14d (a blend of distinct shades 14c and 14e).

During use, the user removes the cosmetic applicator from its packaging, and selects the correct right or left version of the cosmetic applicator, where appropriate. If the applicator comes with cover 72 (see FIG. 7), as taught further herein, the user removes the cover. Grasping handle 10b, the user positions cosmetic applicator 10 (FIG. 1), perhaps feeling the peripheral edge of the applicator contact the eye area, and repositions the applicator as needed. Upon a satisfactory position, the user applies pressure with one or more digits to the rearward surface of substrate 12. The cosmetic utilized in application element 14 is thus transferred to the body of the user. Light pressure may be applied to the applicator directly, in a rolling motion about a finger of the user on the lid and brow, or may be accomplished by lightly massaging or rubbing the rearward surface of the applicator 10. Preferably, at least one of the transferable cosmetics has been formulated to have improved wear quality as will be taught further herein.

Illustrative instructions to the user may be as follows: "With plastic cover facing you, pull one of the eyeshadow sheets away from the plastic and separate. Apply one eye at a time. Align inside of sheet (rounded edge) with the inner corner of eyelid and hold in place. With fingers (of opposite hand), gently press and rub the entire sheet to ensure transfer of the whole look. Remove the sheet and blend with fingertips."

Figure 13:
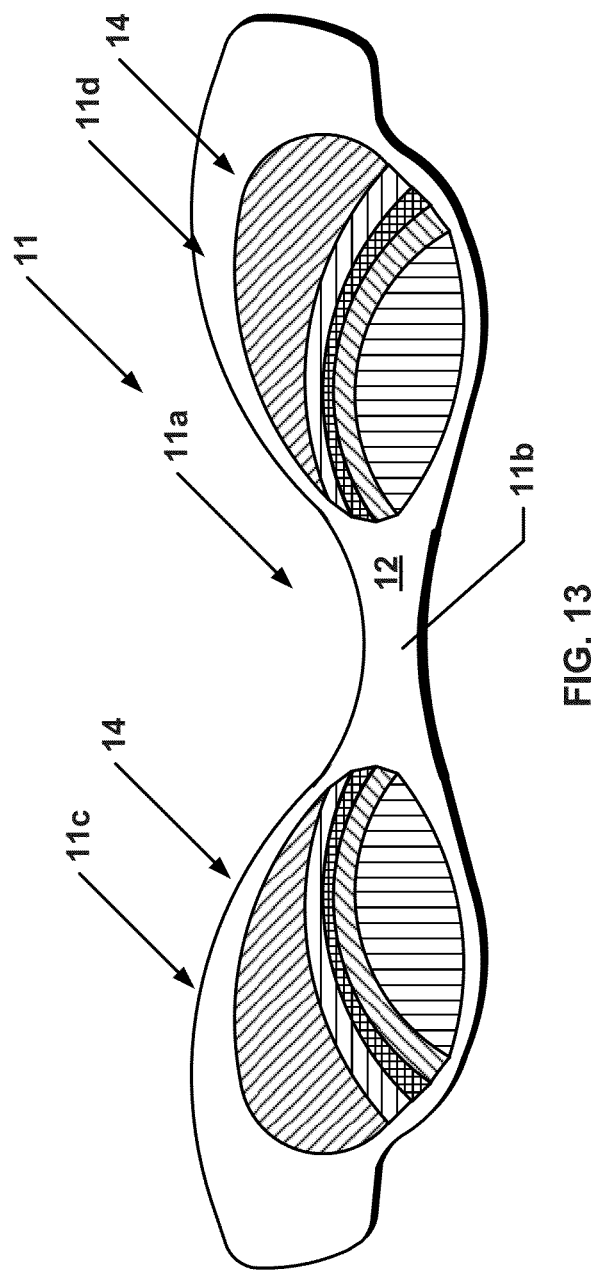
FIG. 13 illustrates a cosmetic applicator in accordance with a further embodiment of the present invention.

In a further embodiment illustrated with respect to FIG. 13, a cosmetic applicator 11 includes two application elements 14 disposed as described above on a substrate 12. Preferably, the application elements 14 are attached to the substrate 12. To provide convenience to the user and to prevent mixing of a right or left applicator, the applicator is configured to have a shape 11a suitable for consecutive application to the left and right eye areas of a user. Shape 11a includes a bridge 11b connecting the left and right eye areas 11c, 11d, respectively wherein appropriately oriented application elements 14 are disposed. Preferably, each application element 14 is removed separately from the substrate 12 and consecutively applied to the eye.

Cosmetic applicator 10 may be manufactured using a flat screen printing process, i.e. serigraphic printing, as illustrated herein and/or as disclosed in U.S. Pat. No. 5,192,386, which is incorporated by reference in its entirety herein. However, cosmetic applicator 10 may also be manufactured according to any other suitable process.

Figure 5:
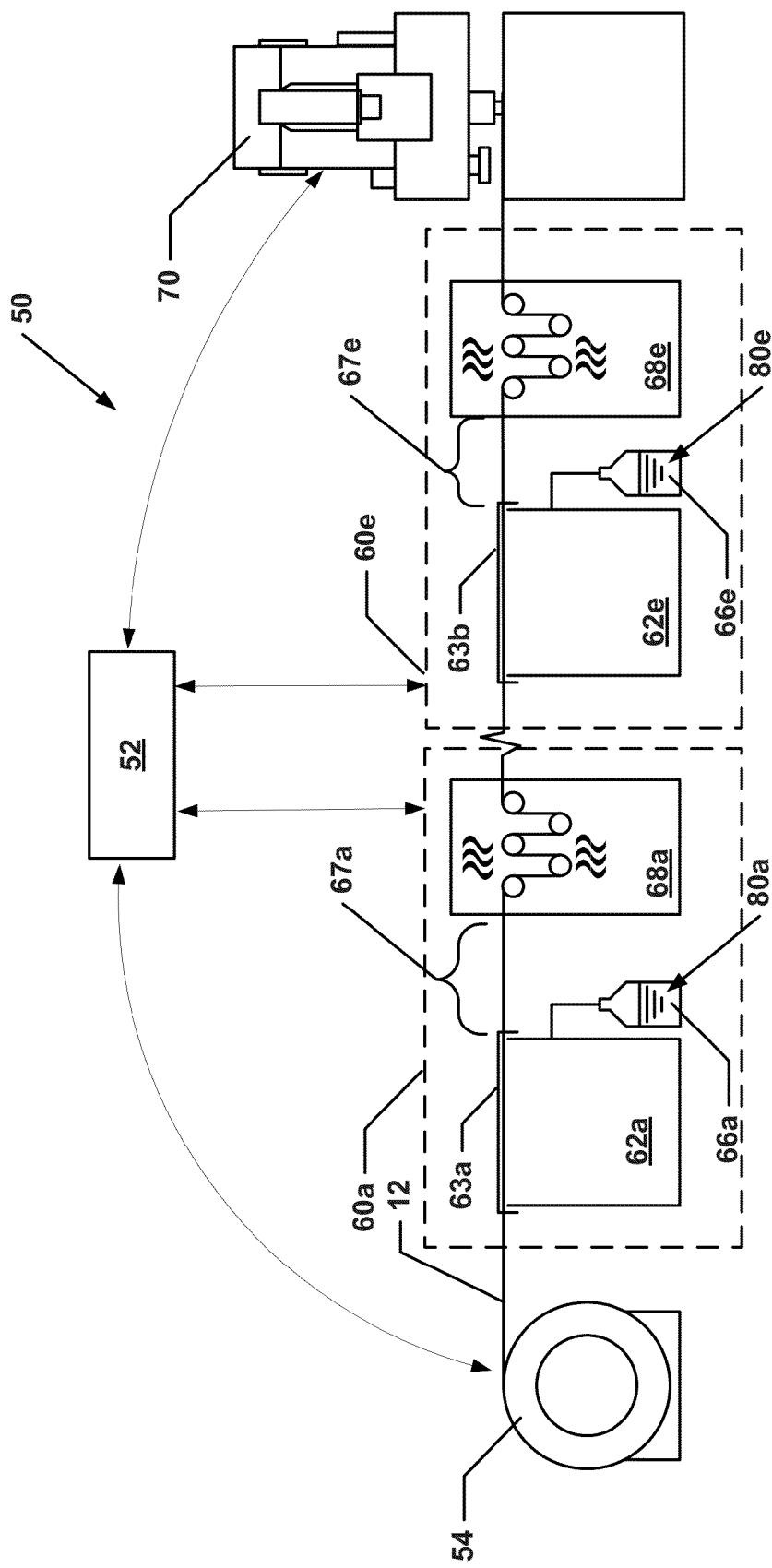
FIG. 5 illustrates a schematic view of the method of manufacture of a cosmetic applicator in accordance with another embodiment of the present invention.

Referring to FIG. 5, a system 50 may include a controller 52, a supply of substrate, generally indicated as 54, a plurality of screen printing units, indicated generally as 60a and 60e, and a finishing operation, generally indicated as 70. Substrate 12 is preferably provided on a roll 54 or may be provided on sheets or the like. Under the embodiment of FIG. 5, the substrate passes through a plurality of screen printing units which deposit the cosmetic composition serially in predetermined application areas on the substrate, to form one application element. The manufacturing is completed when the cosmetic applicator is suitably sized and packaged. More specifically, screen printing unit 60a applies a cosmetic to form a first application area 14a of the application element 14 onto the substrate and prepares it for a subsequent manufacturing step.

As illustrated in FIG. 5, screen printing unit 60a includes a printer 62a having a screen 63a prepared as is generally known in the art. As shown in FIG. 6, screen 63a comprises an impermeable surface having one or more screened apertures 64a in the surface that correspond to the shape and size of application area 14a. Subsequent screens (63b-63e, screens 64c, 64d, were omitted in the illustration for the purposes of clarity) will have different apertures (64b-64e) that correspond to the shape and size of their respective application areas further illustrated in FIG. 7 (14b-14e). A plurality of targets 65 on the screen and the substrate may be provided to aid in the precise positioning and printing of the application area.

Referring back to FIG. 5, a reservoir 66a provides a suitable amount of slurry 80a to screen 63a and a suitable portion exits through screened aperture 64a onto the substrate to create application area 14a. After application area 14a has been deposited, the excess slurry is removed. The screen is removed and the substrate travels a distance 67a to a dryer 68a.

The distance is preferably predetermined to permit the evaporation of some or all of the solvent from the composition for application area 14a and may be adjusted with respect to differences in composition. Distance 67a may instead be configured as drying rack wherein the roll stock or sheet stock of substrate 12 remain for a predetermined time to suitably evaporate the solvents. Dryer 68a may be any suitable dryer to accommodate the roll stock or sheet stock of substrate 12 and to dry the composition deposited as application area 14a.

In the embodiment of FIG. 5, one or more further screen printing units (60e) are provided to print application areas 14b-14e. In each respective screen printing unit, an appropriate slurry (80e) is selected to be deposited for each application area via screened aperture (64e) and screen (63e). For example, if 5 application areas (14a-14e) are desired, the first application area 14a would preferably be processed by a first screen printing unit 60a, and subsequent application areas (14b-14d) would be processed by further screen printing units utilizing their respective slurries (not shown). The final (5th) application area 14e would be processed by screen printing unit 60e (using slurry 80e) as illustrated in FIG. 5.

After processing by screen printing units (60a-60e), the printed roll stock or sheet stock then passes to finishing operation 70 where it is preferably cut in one or more steps in a cutter so that cosmetic applicator 10 has shape 10a as illustrated in FIG. 1. In the same step or in a different step, a cover 72 is cut to suitable shape or provided to prevent errant removal of the application element. Preferably, the cover is cut to match shape 10a and/or to permit easy identification is transparent or clear. For example, cover 72 may be made of a clear plastic laminate. The cosmetic applicator is then packaged for delivery. During finishing operation 70, the product may be cut into sheets and these sheets may be sent to a separate offline operation to be cut in the shape shown in FIG. 13.

With respect to the previous figures and now FIGS. 8-12, in accordance with further embodiments, one or more screens may be configured to coordinate apertures with the substrate such that an application area such as Detail C (FIG. 8) may be selectively printed in some, but not all reservoirs. Thus, screen 63i illustrated in FIG. 9 will produce an application area 14i (FIG. 8) having cosmetic material deposited only in a selected portion thereof. In this manner, it is possible to control the effect of the cosmetic. It is also further possible to overlay screens to blend effects. Thus, screens 63g and 63h are suitably configured to sequentially overprint each other to achieve application area 14g in the location of Detail D.

In one or more embodiments, area 14g is achieved by using a single screen and formulating the slurry to be a predetermined blend, typically a 50-50 blend, of the respective adjacent area slurries. The slurry may also be a mix of the three primary shades in a predetermined ratio.

The cosmetic composition is formulated so that it has a greater affinity for the skin than the substrate. It has been found that the transfer of the cosmetic from the substrate around the eye area is improved when the composition contains a filler such as mica having a platelet crystalline structure. It is believed also that transfer is facilitated around the eye area because the skin around the eye has a higher concentration of natural oils.

Consequently, to optimize the transfer of cosmetic to the skin, one might need to reduce the amount of transfer of the powder onto the eye. Additionally, a readily transferring powder cosmetic can be loose enough to get dusted out of their printed zones because of vibration forces during processing or shipping of the product. A reduction in transfer is achieved by increasing binding forces by either adding liquid binder to the slurry that improves powder to powder and powder to paper binding.

The cosmetic slurry (80a-80e) preferably comprises the cosmetic composition and one or more non-aqueous volatile solvents into which the cosmetic composition is dispersed. The cosmetic comprises 35 to 65%, preferably 40 to 60% by weight make up of the slurry and may be a blended powder as is generally known in the art.

The solvent that permits the slurry to flow may be odorless mineral spirits, isopropyl alcohol, volatile silicones, or the like or compatible combination thereof into which the cosmetic composition is added. The quantity of solvents is preferably adjusted to accommodate the density of the screen mesh. Also useful as the volatile solvent is water or water in compatible combination with another solvent such as a low molecular weight alcohol such as isopropyl alcohol or ethanol.

Thus, additional solvent may be added to decrease viscosity and improve flowability. The slurry may also be made more viscous and reduce flowability by reducing the solvent relative to the cosmetic. The volatility of the solvent is predetermined to ensure its substantial removal during the drying step in the manufacturing system.

Preferably, to prevent separation of the slurry, the slurry is continually mixed in the reservoir 66. To further stabilize the slurry, a suspending agent may be incorporated into the slurry to help suspend the cosmetic ingredients in the volatile solvent. The suspending agent may be volatile and/or hydrophilic. Suitable suspending agents may be surfactants such as glyceryl esters, ethoxylated fatty alcohols, phospholipids such as lecithin, and the like, and combinations of such materials. Non-surfactants such as maltodextrin or modified cellulosics may also be used. Certain ingredients listed below in the discussion of fillers, for example, bentonite, may assist in suspending the powders in the volatile solvent. Lecithin is preferably added as a suspending agent to the cosmetic slurry. The suspending agents is incorporated into the slurry in a range of from 0 to about 10% preferably from 0 to about 5%, by weight of the solvent present in the slurry.

The cosmetic composition preferably comprises, based on the weight of the cosmetic composition:

(1) one or more pigments and/or pearlescents in an amount and in a predetermined combination to provide the desired color effect, preferably in an amount of from about 0.1 to about 80%, preferably from about 1 to about 60%, and most preferably from about 5 to about 45%, (2) one or more dry binders in a range of from 0 to about 15%, preferably from about 1 to about 12%, and most preferably from about 2 to about 9%, (3) one or more wet binders such as oils in a range of from 0 to about 25%, preferably from about 2 to about 20%, and most preferably from about 3 to about 10%, (4) one or more fillers, typically from 0 to about 95%, preferably from about 10 to about 85%, and most preferably from about 15 to 65%, and (5) preservatives in an antimicrobially effective amount, typically in the range of 0 to about 5%, preferably from about 0.05 to about 3%, and most preferably from about 0.1 to about 2%, with the total of dry and wet binders being at least about 0.5%, preferably at least about 1%, and most preferably about 4% and above.

The pigments and pearls can be any pigment or pearl typically used in cosmetic compositions, in particular in an eye shadow cosmetic. The pigments can be coated or otherwise treated as is common with pigments used in the cosmetic field to improve dispersability as well as improve wear. Illustratively, one or more suitable pigments may be selected from the groups of:

1. Ultramarines;
2. Titanium pigments such as titanium dioxide, titanium dioxide on mica, or the like;
3. Ferrocyanides such as ferric ferrocyanide, ferric ammonium ferrocyanides, or the like;
4. Iron oxide pigments such as black, brown, red, and yellow iron oxides;
5. Drug and Cosmetic grade organic colorants such as dyes and lakes such as: Blue Lake 1, Yellow Lake 5, Red lake 40, Yellow No. 5 aluminum lake, Yellow No. 6 aluminum lake, Red No. 6 barium/strontium lake, Red No. 7 calcium lake, Red No. 7 calcium lake, Red No. 27 aluminum lake, Red No. 30 lake, or the like;
6. Carmine;
7. Manganese violet; and
8. Chromiums such as chromium hydroxide green, chromium oxide green, or the like.

Pearlescents are natural or synthetic, and typically are pigment coated mineral substrates. The pigments are usually iron oxide (black, red, yellow, or brown), titanium dioxide and carmine. The substrates include mica, synthetic flurophlogopite, calcium borosilicate, bismuth oxychloride, and aluminum oxide. Suitable pearlescents may be mica, coated with a titanium dioxide or iron oxide, bismuth oxycholride coated with titanium dioxide, and the like. Additionally, materials such as terephthalate compounds may be incorporated in the cosmetic composition to provide a glitter appearance.

The pigments and pearlescents can be used singly or in any combination to provide a predetermined shade or cosmetic effect. For a frost shade, pearlescent materials are included in the cosmetic composition, along with pigments to provide the desired shade. Cream shades, on the other hand, typically contain predominantly only pigments, with the pearlescent concentration being less than about 10% by weight of the cosmetic composition. Care must be exercised to select a pigment that is approved for use in the application of choice. For example, Red No. 27 aluminum lake is not approved in the U.S. for use in eye make-up.

The liquid, semi-solid, or solid binder aids in adhesion of the cosmetic to the substrate and to itself to prevent dusting.

One or more suitable dry binders may be selected from the groups of:

1. metal salts of fatty acids, for example, stearates such zinc stearate, aluminum stearate, calcium stearate, lithium stearate, magnesium stearate, and myristates such as zinc myristate, aluminum myristate, magnesium myristate, or the like;
2. waxes such as carnauba wax, beeswax, synthetic wax, microcrystalline wax, polyethylene wax, or the like;
3. polyethylenes;
4. methacrylates such as methyl methacrylate, polymethyl methacrylate, or the like;
5. kaolin;
6. lysine such as lauroyl lysine;
7. boron nitride;
8. fatty alcohols such as cetyl alcohol, stearyl alcohol, eicosanol, or the like; and
9. bismuth oxychloride.

One or more suitable wet binders may be selected from the groups of:

1. esters such as isostearyl neopentanoate, isostearyl hydroxystearate, octyldodecyl stearoyl stearate, glyceryl esters, coco-caprylate/caprate; caprylic/capric triglyceride, sterol esters, PPG-1 isoceteth-3 acetate, or the like;
2. silicones, e.g., dimethicone, dimethiconol, trimethylsiloxysilicate, dimethyl/trimethyl polysiloxane, and the like;
3. nonvolatile hydrocarbon oils such as mineral oil, polyisobutenes, petrolatum, and the like;
4. natural oils such as squalane, coco butter, shea butter, vegetable oils such as jojoba oil, and the like;
5. polyols such as glycerin; and
6. polymers such as polyurethanes, polyacrylates, etc. The wet binders are generally lipophilic and may be liquid or as in the case of petrolatum a semi-solid. The binders are provided in an amount effective to maintain the cosmetic composition on the substrate and to also cause the cosmetic composition to be retained preferentially on the skin when it is applied using the applicator.

One or more fillers (also referred to as bulking agents) is provided in the slurry preferably in the form of a low density powder to soften up the powder and reduce the compaction of the cosmetic. The fillers are typically inert powders but preferably can be selected to optimize the organoleptic and application properties of the cosmetic as applied to skin. In this regard, fillers such as silica, polyethylene, alumina, polymethyl methacrylate, boron nitride, nylon, and the like that have a spherical particle size improve feel, enhance optical properties, and facilitate application to skin. Therein, the fillers assist the cosmetic in transferring from the substrate to the body of the user. One or more suitable fillers may be selected from the groups of:

1. talc;
2. mica;
3. synthetic fluorophlogopite;
4. sericite;
5. corn starch;
6. clays, such as bentonite and kaolin;
7. bismuth oxychloride;
8. calcium silicate;
9. calcium carbonate;
10. nylon powder, such as extra fine nylon powder;

11. polymethyl methacrylate;
12. polyvinylidene copolymers;
13. barium sulfate;
14. silica and alumina;
15. sterilized silk powder;
16. polyethylene;
17. boron nitride; and
18. calcium borosilicate.

Therein, one or more suitable preservatives may be incorporated. These maybe selected from the groups of parabens such as methyl paraben, ethyl paraben, propyl paraben, butyl paraben, or the like; and caprylyl glycol.

The cosmetic composition may also include one or more active ingredients present in an amount effective to achieve its intended function. The active ingredient may be a sunscreen, a film former, a fragrance, antioxidants, chelating agents such as sodium ethylenediamine tetraacetic acid, vitamins, optical blurring agents, and emollients.

Typically, the cosmetic active is present in an amount of from 0 to about 10%, preferably from about 0.1 to 5% by weight of the cosmetic composition. Many sunscreens such as ethylhexyl methoxycinnamate have an oily consistency, and, thus, have properties of a wet binder. Oily actives such as sunscreens that have wet binder properties are included in the wet binder premix and their concentration in the cosmetic composition is included in the wet binder concentration as described above.

All the above are generally available from commercial sources such as Atofina, BASF, Dow Chemical, Celanese, Rohm and Haas, Mitsubishi Rayon, Presperse, Kobo, Noveon, ISP, Sensient, Rona, or Sumitomo. Cosmetic ingredients suitable for use in the cosmetics of the present invention are identified in the International Cosmetic Ingredient Dictionary and Handbook (INCI), Vol. 3, Section 3 (11th Edition 2006) published by the Personal Care Product Council (formerly known as the Cosmetic, Toiletries and Fragrance Association (CTFA)) incorporated herein by reference thereto.

Eye Shadow Applicator

The cosmetic composition of Table 1 is prepared by mixing the fillers, pigments (excluding pearls), powder binders, and preservatives to form a powder premix. A premix of the wet binders is also prepared, and the powder premix is combined with about 70% of the wet binder premix, followed by processing in a hammermill. The pearls and remaining wet binder is then added with mixing.

TABLE 1

| COMPONENTS | Amount (Wt. %) |
|---|---|
| Fillers | |
| Talc | 40 |
| Sericite | 8 |
| Polymethyl methacrylate (spherical) | 2.5 |
| Bismuth oxychloride | 1.5 |
| Corn starch modified | 5 |
| Total Fillers | 57 |
| Pigments/Pearls | |
| Iron oxide (mix of black, red and yellow) | 1.15 |
| Ultramarine blue | 0.5 |
| Pearlescents (iron oxide, titanium dioxide, and carmine coated micas) | 32.15 |
| Total Pigments/Pearls | 33.8 |

TABLE 1-continued

| COMPONENTS | Amount (Wt. %) |
|---|---|
| Dry Binders | |
| Zinc stearate | 1 |
| Kaolin | 2 |
| Total Dry Binders | 3 |
| Wet Binders | |
| Octyldodecyl stearoyl stearate | 2.5 |
| Isostearyl neopentanoate | 2.5 |
| Ethylhexyl methoxycinnamate (sunscreen) | 0.6 |
| Total Wet Binders | 5.6 |
| Preservatives | |
| Tetrasodium EDTA | 0.1 |
| Methylparaben | 0.3 |
| Butylparaben | 0.2 |
| Preservatives | 0.6 |

With reference to FIG. 5, a mixture is described: fifty parts, by weight of the cosmetic composition set forth in Table 1, is admixed with fifty parts odorless mineral spirits to form slurry 80a, which is charged into supply drum 66a. Similarly, suitable cosmetic compositions having different shades are formulated, admixed with volatile solvent to form slurries 80c and 80e, and charged into supply drums 66c and 66e. The slurries 80b and 80d for charging into supply drums 66b and 66d may be prepared, respectively, by mixing slurry 80a with slurry 80c on a 1:1 weight ratio, and by mixing slurry 80c with slurry 80e on a 1:1 weight ratio. Alternatively, the three primary powder compositions may be admixed to form the blended shades, or new compositions may be prepared for the blended shades. Alternatively, slurries 80a and 80c (and 80c and 80e) can be admixed in line before dispensing onto the screen.

The substrate is fed into system 50, specifically into each screen printing unit 60a through 60e, and each of slurry 80a through 80e is dispensed independently through each of screens 63a through 63e and onto substrate 12. The roll of substrate 54 is processed in this fashion with cutting and packaging taking place in the finishing unit 70 to provide applicators conforming to the applicator 10 shown in FIG. 1.

A right eye applicator is applied to the area above the right eye of a user by pressing the applicator cosmetic side down, with the forefinger providing moderate pressure to this area in a rolling a stroking, or rubbing motion, thereby transferring a unit dose of the cosmetic compositions from the substrate to the area, with five different color shades of cosmetic composition 14a through 14e being visible. This procedure is repeated for the left eye using the left eye applicator.

The description provided above is thus applicable for eyeshadow applicators, as well any other products suitable for cosmetic application, such as face powder, blush, powder color correctors or bronzers.

Under an alternate embodiment, a cosmetic product may be produced using a screen printing process which has been described above using soft, flexible, typically thin, paper as a substrate 12. However, prior to processing, a laminated web may be loaded, where the lamination comprises a carrier board for support. Preferably, the carrier board should have a thickness of about 0.003 to about 0.012 inches, and most preferably about 0.008 inches. It is understood that the carrier hoard may or may not be necessary if the paper is able to be self supporting. Nevertheless, if the carrier board is used, the board preferably has a thinner, softer face for mating with the paper. The carrier board may also be comprised of a nonwoven or other material. An adhesive is preferably applied to the face of the board to allow proper mating. However, the adhesive should have a sufficiently low tack to allow the board to be removed easily and leave no or minimal residue to the soft/flexible paper.

A preferred adhesive is a low tack pressure sensitive adhesive that is applied to the carrier board for mating with the paper. The adhesive should not transfer to the paper. The pull forces for the adhesive should preferably be between 0.10 to 0.20 lbs. This force was measured as follows: A 2×4 inch strip is pulled apart at a speed of 12 inches per minute using an Instron or like device and the reading is the maximum force point to separate the soft, thin paper from the backing or carrier. It is not a cumulative force across the entire sample, but rather represents a "toughest point of force" value. Marginal forces are specified at 0.21 to 0.30 lbs of force. Forces above 0.30 lbs are considered unacceptable as the soft paper and the carrier board will be difficult to remove at the end of the process and may result in tearing of the cosmetic product.

Figure 15:
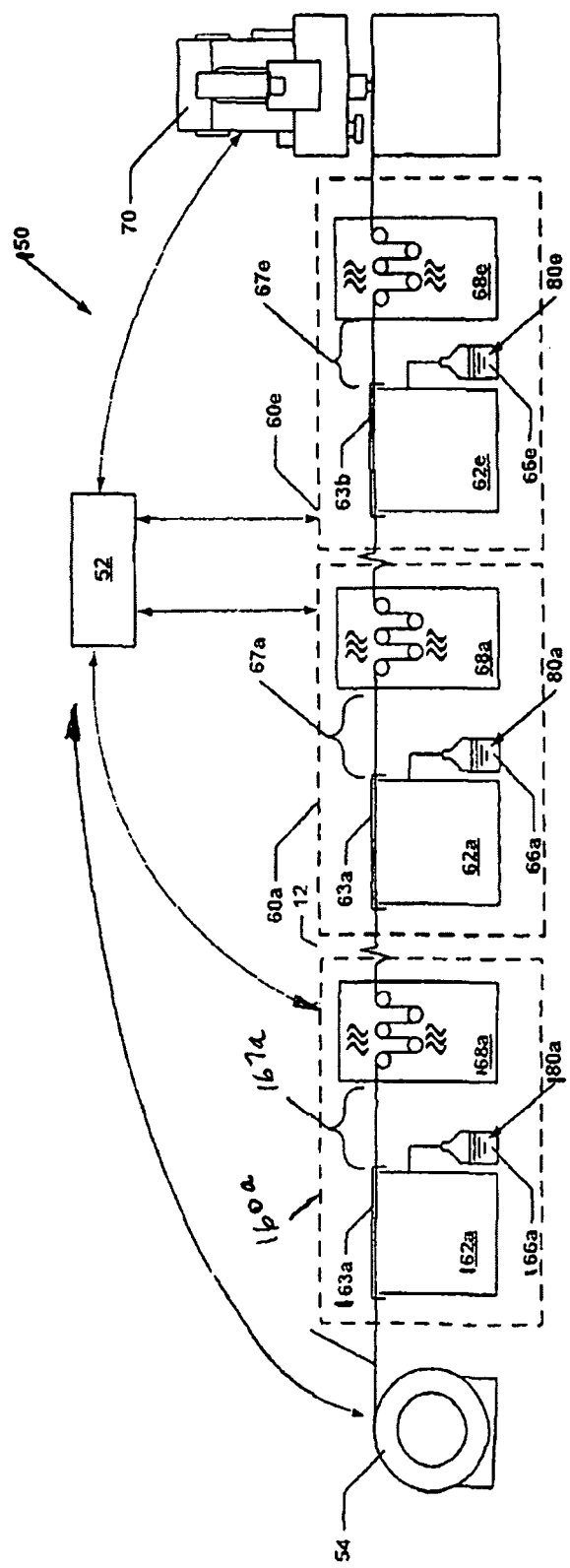
FIG. 15 illustrates a schematic view of the method of manufacture of a cosmetic applicator in accordance with another embodiment of the present invention.

A screen printing station 150 (see FIG. 15), used for processing the cosmetic applicator under the present embodiment, includes a screen printing unit 160a for printing a wetting agent 180a through a screen 163a onto the surface of the paper. Screen printing station 150 of FIG. 15 is similar to the screen printing station 50 of FIG. 5, except that screen printing station 150 comprises printing unit 160a for printing wetting agent 180a in addition to the plurality of screen printing units 60a-60e. There may or may not be some absorption of the wetting agent 180a (dispensed from reservoir 166a) into the supporting board stock depending on the thickness of the soft material. The wetting agents in the present embodiment are distinguished from suspending agents added to cosmetic slurries as previously discussed. The wetting agents described herein are used to prepare the surface of the paper to accept the cosmetic slurry by pre-wetting the surface. By applying the wetting agent, the application advantageously prevents screen clogs and provides a more even surface for printing on the paper. The wetting agent is particularly advantageous for any soft, flexible, thin, and/or porous type paper, non woven, or laminate. Preferably, the wetting agent is volatile, and will typically substantially evaporate from the flexible substrate during the drying step disclosed below. The wetting agent preferably also is hydrophilic, and is miscible with water.

The wetting agent 180a typically comprises a low molecular weight polyol or mixtures of two or more of such polyols having from about 2 to about 8 carbons, preferably diols of 3 to 6 carbons. The wetting agent may further contain small amounts of a volatile varnish material (e.g., modified cellulosics such as nitrocellulose) to adjust volatility of the wetting agent mixture. The wetting agent may also comprise silica and/or other compatible thickeners. Preferably, the wetting agent comprises about 50.5% Dipropylene Glycol, about 44.5% Propylene Glycol, about 2.7% Silica, and about 2.3% medical grade varnish, where the vapor pressure of the Dipropylene Glycol is 0.016 mm Hg, 25° C., and the vapor pressure of the Propylene Glycol is 0.0129 mm Hg, 25° C. The medical grade varnish may be a modified cellulosic that is alcohol based (e.g., a nitrocellulose modified by shellac). Preferably, the wetting agent is printed in a pattern that covers the shape of the cosmetic prints and the adhesive, with an additional ⅛" surround to allow for print variability.

The wetting agent will at least partially evaporate during the printing process, but should not permit the subsequent cosmetic prints to bleed outside of the desired artwork. Referring to the formulation given above, the Dipropylene Glycol and Propylene Glycol essentially evaporate during processing. Non evaporating materials such as silica can be used to increase the viscosity of the wetting agent. Numerous combinations of raw materials, thickening agents in various percentages are possible. The wetting agent station allows the material to absorb it and then the cosmetic powders can be printed on top.

After it is initially applied, the wetting agent may be dried slightly, under temperatures ranging from room temperature to about 150° F., preferably about 77° F., depending the formulation and other environmental conditions. The process then continues through a perforating unit that places a dual perforation into each sample. The perforation should be of an appropriate size and depth to allow the sheets to be separated by the user during application.

The first of several cosmetic slurries is printed onto the pre wetted soft material and dried slightly to evaporate some of the solvent in the cosmetic slurry and make the surface of the colored print less likely to transfer and pickup onto the next color. Drying temperatures are from room temperature (e.g., about 60° F.) to about 150° F., preferably about 140° F., depending on the formulation, speed of the system and other environmental conditions.

The next cosmetic color for the colored print is printed immediately adjacent to the first printed color in a side-by-side manner. A "make-ready" is made in-pattern to pull away the previously printed color and keep it from touching the surface. The make-ready may be a thin stencil that has a cut-out corresponding to a previously printed area. When a second area is to be printed, the make-ready is placed on the vacuum table. The carrier board and substrate would then be placed on the make-ready so that the previously printed area is pulled toward the table. A screen for the second area to be printed is placed on the substrate and the second area is printed. Thus, by having the previously printed area recessed due to the vacuum, the chance of overprinting and smudging is reduced. The board is then run through a dryer with temperatures ranging from room temperature to about 150° F., preferably about 110° F., depending on the formulation, speed of the system and other environmental conditions.

The artwork is preferably designed with almost zero tolerance. In other words, the colors touch each other as exactly as possible with no overlap. None of the base soft paper shows between two colors as they are printed. Since there can be some slight movement in the paper or expansion due to the wetting of the paper, it is sometimes necessary to increase the artwork slightly, about 1/32 to 1/64" to allow for this expansion. This may result is a very slight overlap which prevents any of the paper from showing through and distorting the artwork. Additional cosmetic colors are printed depending on the artwork complexity using further "make readies" to pull away the cosmetic colors that have already been printed.

After all cosmetic colors are printed, the board is run through dryers to evaporate the volatile wetting agent components and solvents from the cosmetic slurries, to leave only the cosmetic powder in the correct position. The next screen prints an adhesive and also contains a "make ready" that pulls the entire cosmetic printed artwork away from the bottom surface of the screen so that it does not get damaged while the adhesive is being printed.

When applying adhesive, it should be printed in a pattern that allows the deposit to be in an area of the substrate not printed with cosmetic, i.e., outside the area of the application elements, e.g., in an area between the eyes in an area that will hold the paper substrate to the protective layer superposed on top of the paper (e.g., approximate bridge 11b in FIG. 13).

The protective layer will be applied over the adhesive to removably affix the paper to the protective layer, thereby protecting the cosmetic powder. The protective layer is preferably of a clear polyester type that is 4 or 2 mm thick. This layer can also be a poly material, paper, biopolymer, or any other material that would cover and protect the powder. The adhesive may also be printed on the outside of the cosmetic applicator to allow excess from the paper and protective layer to be held together when the applicators are die cut and the matrix is removed. After application, the adhesive is dried slightly with temperatures ranging from room temperature to about 180° F., depending on the adhesive formulation, amount, and environmental conditions. The preferred adhesive is water-based indirect food contact type. Directional indicia may be printed on the protective layer to indicate to the consumer the proper orientation of the cosmetic applicator.

The backing paper can then be removed by separating the board from the soft paper which is covered with the protective layer or it can be removed after the sheets have been cut and removed from the press. If it is removed on press, the top protective layer and the paper with the cosmetic print are separated from the carrier board by starting the separation and pulling them apart having the bottom board layer roll up underneath the press and the top layer cut into sheets. The sheets are moved to a separate finishing operation where they are die cut into the desired shape and placed into trays with lids and boxed.

The cosmetic screens under the present embodiment are made using Max R emulsion, where the screens range from 110 to 180 mesh. The screens are preferably coated twice on the side that makes contact with the web and once on the squeegee side. The wetting agent screen is preferably coated with Kiwo™ Poly-Plus emulsion and each side is coated once. The wetting agent screen ranges from 380 to 540 mesh.

Blush Applicator

Figure 14:
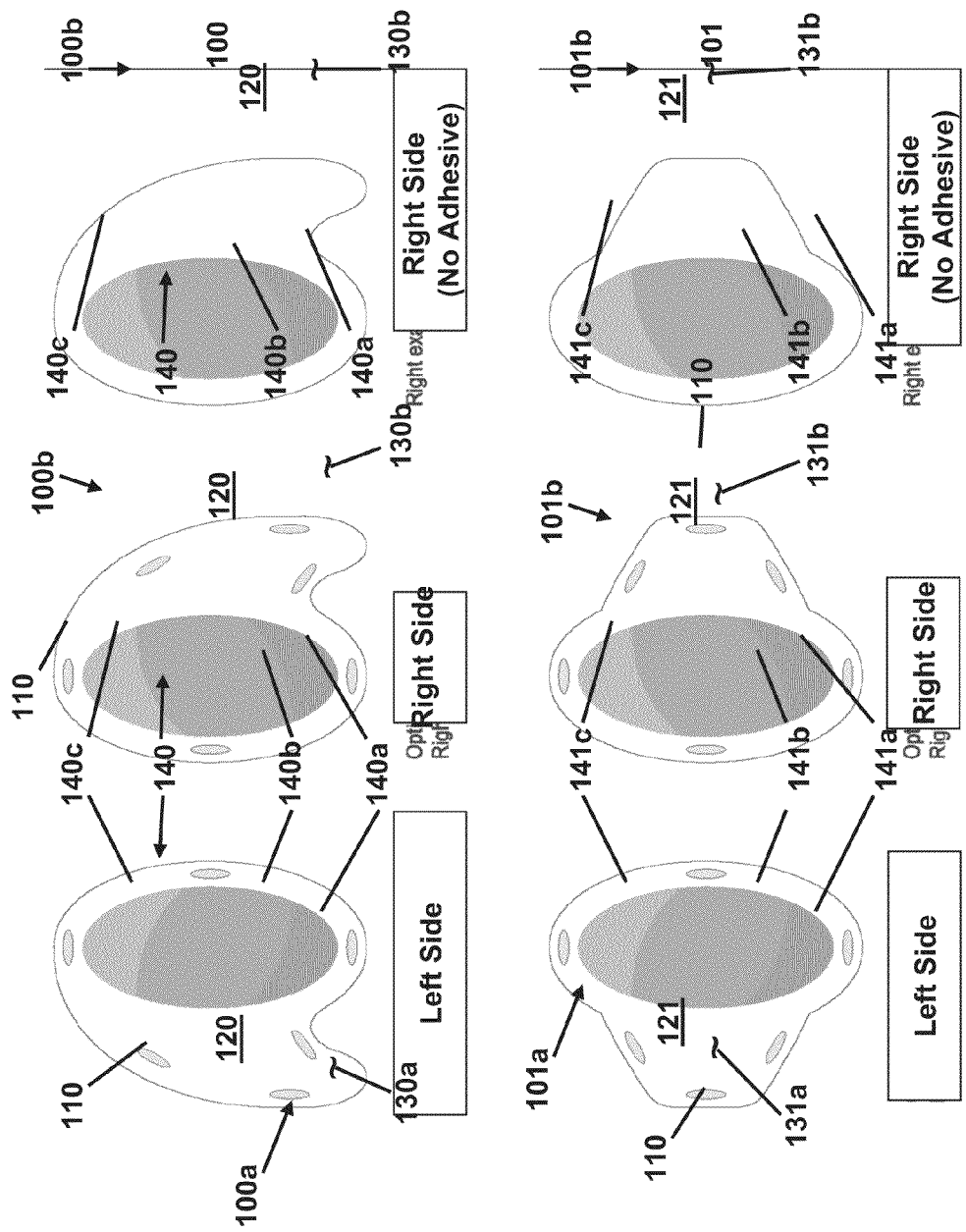
FIG. 14 illustrates a blush cosmetic applicator in accordance with one or more embodiments of the present invention.

Referring now to FIG. 14, yet another embodiment is illustrated for blush applicators (100, 101) that are processed in a substantially similar manner as the eye shadow embodiment discussed above in connection with FIGS. 1-13 and 15. Cosmetic applicator 100 is illustrated having two shapes: a shape 100*a* appropriate for the left side of a face, and a shape 100*b* appropriate for the right side of a face. Substrate 120 preferably comprises a flexible planar body manufactures to encompass substantially the entirety of each respective shape (100*a*, 100*b*) to support application element 140. The material is preferably a soft, flexible paper that has sufficient tensile strength to withstand processing. As with substrate 12, described above, substrate 120 may be comprised of numerous other materials as well.

Application element 140 comprises a plurality of cosmetics disposed substantially in a thin layer on a frontward surface of substrate 120. The application element 140 comprises a pattern of one or more application areas, generally indicated as 140*a*-140*c* in FIG. 14. The application areas are preferably adjacent to each other in a gapless manner to comprise a coordinated effect or enhancement. The thin layer of cosmetic is configured to be cohesively maintained on the substrate in light of the presence of wet and dry binders, as discussed above. The size of each application area 140*a*-140*e* is preferably predetermined to provide a favored arrangement or to provide a coordinated effect and further permit ease of use for the user.

The cosmetic composition for each application area 140*a*-140*c* is substantially the same as the formulation described above with respect to pigments/pearlescents, wet/dry binders, fillers and preservatives. Under the blush applicator embodiment, the cosmetic composition is preferably different in texture compared to the eye shadow applicator embodiment. During application, the eyelid has a tendency to crease the eye color, which is not a typical problem for a blush application. Accordingly, the blush applicator cosmetic composition is preferably oilier (wetter) than the eye shadow composition. Of course, the blush applicator cosmetic composition may be composed of powders like the eye shadow composition for those with oily skin, or if the blush is applied over a moisturizer or foundation.

Under one embodiment, the lightest shade 140*c* would be placed in an area of the application element 140 that corresponds to the cheekbone, followed by darker shades (140*b*, 140*a*) that descend down the cheek. The light shade assists the user for ensuring proper placement of the cosmetic applicator. During application, the user would grasp the applicator 100 using handles 13*a* (or 13*b*), where the tab would face the ear in a vertical position. The user would then slide the applicator across the cheek. Subsequent blending would be done by the fingertips, resulting in a more contoured and/or defined cheek.

Cosmetic applicator 101 is identical to applicator 100, except that a different shape (101*a*, 101*b*) is provided having tabs which a user may grasp using handles 131*a*, 131*b*. The composition of substrate 121 has been discussed above, in relation to substrate 120 of applicator 100, and will not be repeated here for the sake of brevity. For both cosmetic applicators 100, 101, there are illustrated advantageous placements of adhesive 110 for holding a protective cover (not illustrated) over the substrate (120, 121).

It should be understood that the above description is of preferred embodiments of the invention and is included as illustration only, and is not limiting of the invention. Clearly, variations of the cosmetic applicators, and methods for making same would be understood by a person skilled in the art and such variations are included within the scope of this invention as defined by the claims appearing below.

What is claimed is:

1. A cosmetic applicator, comprising:
a flexible paper substrate consisting of a cellulosic material, and having a planar body and formed in a predetermined shape, and
an application element formed on the substrate,
wherein the application element comprises a plurality of cosmetic application areas, each application area comprising a screen printed layer, and each cosmetic application area having deposited thereon a cosmetic composition comprising at least one pigment and/or pearlescent in an amount from about 0.1 to about 80 wt %;
wherein adjacent cosmetic application areas are cohesively maintained on the substrate in a gapless formation in the presence of at least one of wet and dry binders contained in the cosmetic composition,
wherein at least two of the cosmetic application areas have different cosmetic compositions; and
wherein a protective layer is superposed on top of the flexible paper substrate.

2. The cosmetic applicator of claim 1, wherein the total amount of the at least one wet and dry binder is at least about 0.5 wt %.

3. The cosmetic applicator of claim 1, wherein the cosmetic composition comprises a wet binder present in an amount of from about 2 to about 20 wt %.

4. The cosmetic applicator of claim 3, wherein the wet binder is selected from the group consisting of esters of fatty acids, glyceryl esters, silicones, nonvolatile hydrocarbon oils, natural oils, polyols, and polymers selected from the group consisting of polyurethanes and polyacrylates, and combinations thereof.

5. The cosmetic applicator of claim 1, wherein the cosmetic composition comprises a dry binder present in an amount of from 1 to about 12 wt %.

6. The composition of claim 5, wherein the dry binder is selected from the group consisting of metal salts of fatty acids, waxes, polyethylenes, methacrylates, kaolin, lauroyl lysine, boron nitride, fatty alcohols, bismuth oxychloride, and combinations thereof.

7. The cosmetic applicator of claim 1, wherein the cosmetic composition comprises a filler.

8. The cosmetic applicator of claim 1, wherein the flexible paper substrate has a thickness of about 0.0010 to about 0.012 inches.

9. The cosmetic applicator of claim 1, wherein the substrate has a thickness of about 0.0010 to about 0.0040 inches.

10. The cosmetic applicator of claim 9, wherein the total amount of the at least one wet and dry binder is at least about 0.5 wt %.

11. The cosmetic applicator of claim 1, wherein the amount of cosmetic composition provided on each cosmetic applicator area is a unit dose for that applicator area.

12. The cosmetic applicator of claim 1, wherein the protective layer is removably affixed to the substrate with adhesive.

13. The cosmetic applicator of claim 1, wherein the substrate is subjected to a hydrophobic wetting agent in advance of the deposition of each cosmetic composition in the cosmetic application area.

14. The cosmetic applicator of claim 13, wherein the wetting agent comprises one or more low molecular weight polyols having from about 2 to about 8 carbons.

15. A cosmetic applicator comprising:
a flexible paper substrate consisting of a cellulosic material, and having a planar body and formed in a predetermined shape;
an application element formed on the substrate,
wherein the application element comprises a plurality of cosmetic application areas, each application area comprising a screen printed layer, and each cosmetic application area having deposited thereon a cosmetic composition comprising at least one pigment and/or pearlescent in an amount from about 0.1 to about 80 wt %;
wherein adjacent cosmetic application areas are cohesively maintained on the substrate in a gapless formation in the presence of at least one of wet and dry binders contained in the cosmetic composition,
wherein a protective layer is superposed on top of the flexible paper substrate, and
a carrier board supporting the flexible paper substrate, the flexible paper substrate being removably affixed to the carrier board by a low tack adhesive.

16. A cosmetic application kit having component parts for supplying a unit dose of a cosmetic, the kit comprising the combination of:
(a) at least one cosmetic applicator comprising
(i) a flexible paper substrate consisting of a cellulosic material, and having a planar body and formed in a predetermined shape, wherein the substrate is subjected to a wetting agent; and
(ii) an application element formed on the substrate, wherein the application element comprises a plurality of cosmetic application area, each application area comprising a screen printed layer, and adjacent cosmetic application areas are cohesively maintained on the substrate in a gapless formation in the presence of at least one of wet and dry binders, and wherein a first and a second cosmetic application area comprise a different respective cosmetic composition comprising at least one pigment and/or pearlescent in an amount from about 0.1 to about 80 wt %, and are configured to produce a blended effect of the respective cosmetic compositions,
wherein the first and second cosmetic application areas are overlaid to create a further cosmetic application area having the blended effect;
(b) a container for the at least one cosmetic applicator; and
(c) instructions for use of the cosmetic applicator.

17. The cosmetic application kit of claim 16, wherein the substrate has a thickness of about 0.0015 to about 0.012 inches.

18. The cosmetic application kit of claim 16, further comprising a protective layer superposed on top of the substrate to overlay the substrate.

19. The cosmetic applicator kit of claim 16, wherein the protective layer includes indicia to orient the placement of the cosmetic applicator for the user.

20. The cosmetic applicator of claim 1, wherein said cosmetic composition includes a suspending agent.

21. The cosmetic applicator of claim 15, wherein said cosmetic composition includes a suspending agent.

22. The cosmetic applicator of claim 16, wherein said cosmetic composition includes a suspending agent.

* * * * *